United States Patent [19]

Vavrek

[11] 4,293,770
[45] Oct. 6, 1981

[54] X-RAY TABLE FOR OBTAINING LONGITUDINAL AND LATERAL OBLIQUE CARDIOVASCULAR VIEWS

[75] Inventor: Robert M. Vavrek, Waukesha, Wis.

[73] Assignee: General Electric Company, Schenectady, N.Y.

[21] Appl. No.: 99,132

[22] Filed: Nov. 29, 1979

[51] Int. Cl.³ .............................................. G01N 21/00
[52] U.S. Cl. .................................. 250/445 R; 250/454; 250/521; 250/523
[58] Field of Search ............... 250/445 R, 454, 522, 250/523, 521

[56] References Cited

U.S. PATENT DOCUMENTS

| | | | |
|---|---|---|---|
| 3,714,427 | 1/1973 | Reiniger et al. | 250/523 |
| 3,930,164 | 12/1975 | Alexander | 250/523 X |
| 4,024,401 | 5/1977 | Bernstein et al. | 250/523 X |
| 4,024,403 | 5/1977 | Bernstein et al. | 250/445 R |

*Primary Examiner*—Davis L. Willis
*Attorney, Agent, or Firm*—Wheeler, House, Fuller & Hohenfeldt

[57] ABSTRACT

An x-ray image intensifier is mounted over a patient supporting table for moving horizontally, vertically and for tilting about a laterally extending axis to obtain x-ray views on both sides of vertical. An x-ray tube casing is mounted on a base member in a housing below the table for tilting in angular synchronism with the intensifier. The base member is on a vertically movable platform and is rotatable about a vertical axis to enable positioning the focal spot of an x-ray tube in the casing for making oblique as well as longitudinal x-ray views of the heart of a patient on the table.

3 Claims, 8 Drawing Figures

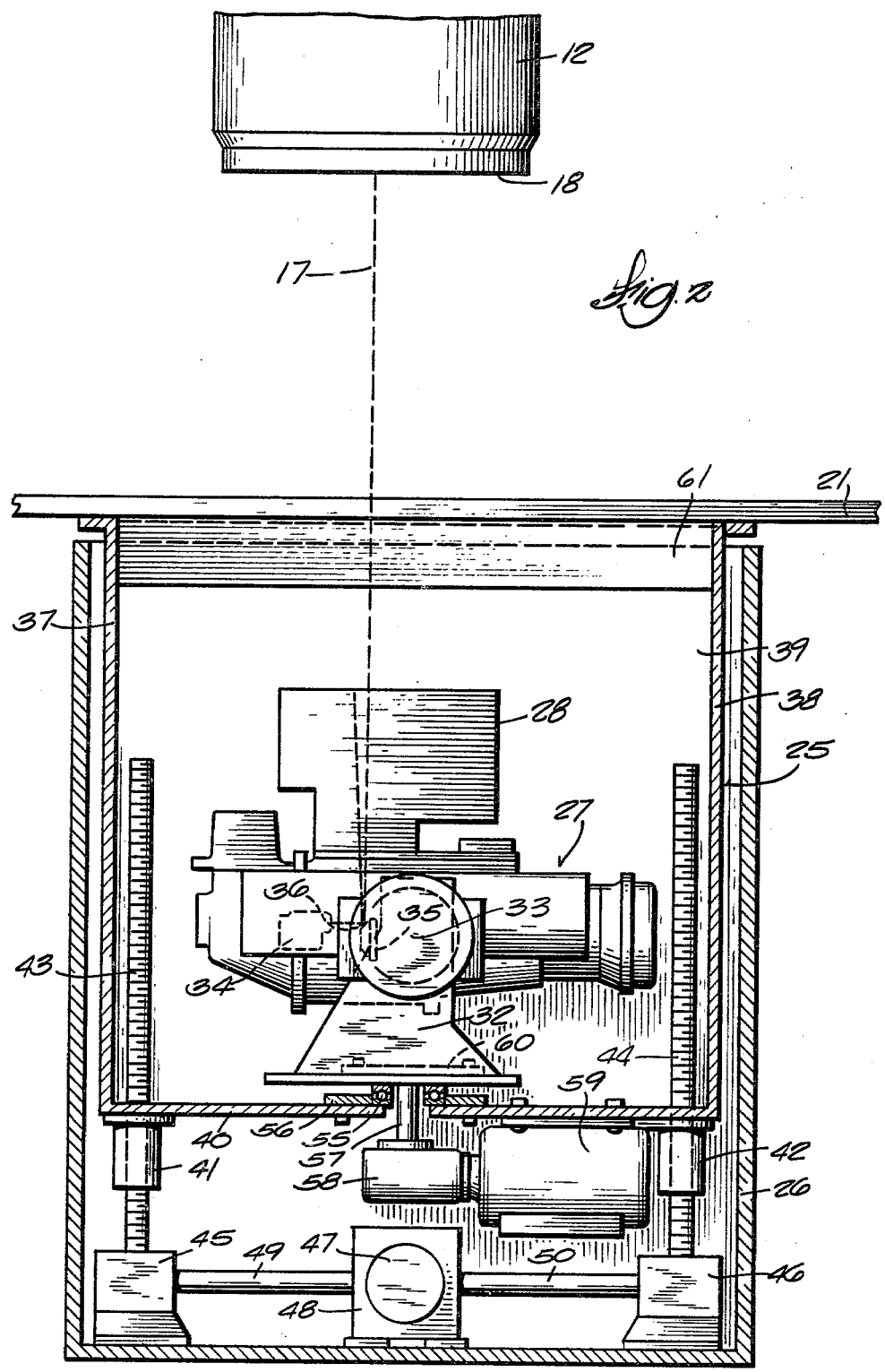

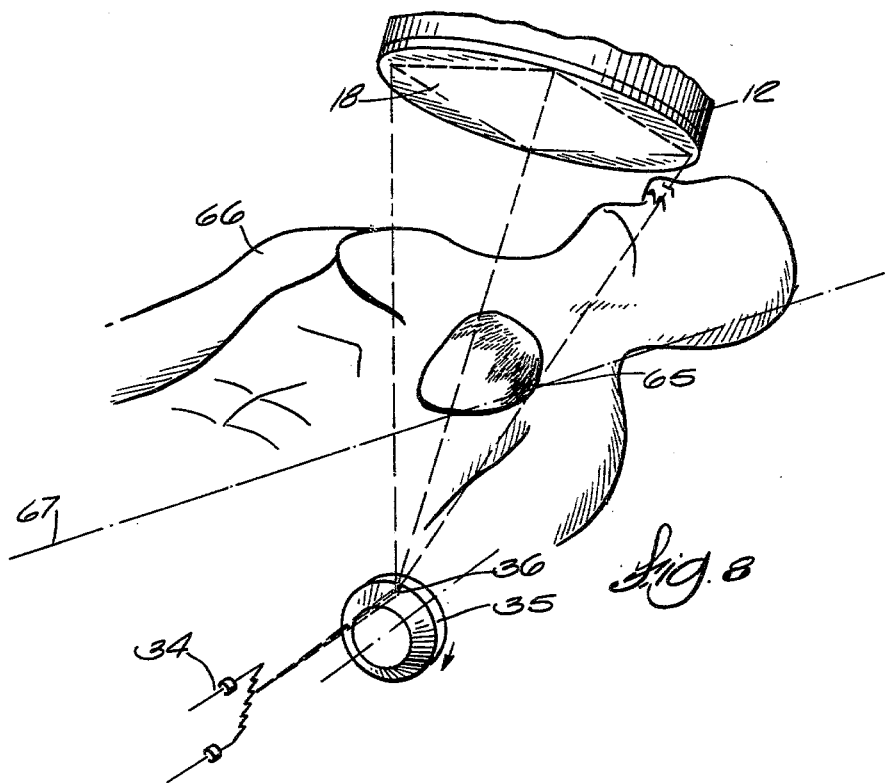

X-RAY TABLE FOR OBTAINING LONGITUDINAL AND LATERAL OBLIQUE CARDIOVASCULAR VIEWS

This invention relates to x-ray cardiovascular examination apparatus.

Typical x-ray apparatus which is adapted primarily for making cardiovascular examinations is illustrated in U.S. Pat. No. 4,024,403. The present invention is an improvement in this type of apparatus. In the patented apparatus, a carriage is mounted for moving on a longitudinally extending overhead track above a patient supporting x-ray table. A vertically extensible arm is mounted to the carriage and a horizontally oriented arm is mounted to the vertical arm. An x-ray image intensifier is mounted on the horizontal arm for pivoting about a laterally extending axis which is perpendicular to the longitudinal direction. The intensifier is thereby adapted for being tilted on the lateral axis for obtaining x-ray views taken at angles through the body.

The x-ray table is supported on a vertically movable housing. An x-ray tube in a suitable casing is mounted within the housing for tilting or angulating about a laterally extending axis in synchronism with the x-ray image intensifier so the central ray of the x-ray beam from the x-ray tube will be perpendicular to the image input plane of the intensifier at all angular positions. Coordinate angulation of the intensifier and x-ray tube permits x-ray views of the heart blood vessels to be taken perpendicularly to the plane in which they lie.

The prior art apparatus under discussion, however, can only angulate the intensifier and x-ray source in a single plane. The arteries of the heart, on the other hand, extend around the heart so it would be desirable if oblique or sideways angulated views of the heart could be obtained.

There is existing x-ray apparatus which allows obtaining a wide variety of oblique views. This apparatus, however, is usually large, heavy and expensive and requires much space in an examination room. Typically, this prior art apparatus has the x-ray image intensifier mounted on one end of a C-shaped arm and an x-ray source on the other end of the arm and a further mounting for allowing the C-shaped arm to be angulated caudally and cranially rotated about the body undergoing examination to enable making x-ray views at any angle. Another prior art approach, particularly applicable to the type of apparatus described in the preceding paragraphs, is to support the examination body on an x-ray table top which can be rotated about a longitudinally extending axis while the patient is strapped into it so that the arterial system of the heart can be viewed at all desired angles, but the method can cause patient discomfort.

SUMMARY OF THE INVENTION

The present invention is an improvement in low cost cardiovascular x-ray examination apparatus of the general type described in U.S. Pat. No. 4,024,403. The improvement comprises mounting the x-ray source for angulating, not only about a laterally extending axis, but about a vertical axis as well. The arrangement is such that the focal spot of the x-ray tube can be orbited about the vertical axis from which it is displaced and angulated longitudinally and elevated to provide an oblique view capability.

A more complete description of how x-ray cardiovascular examination apparatus is modified to achieve oblique view capability will now be set forth in reference to the drawings.

DESCRIPTION OF THE DRAWINGS

FIG. 2 is a vertical section of a housing which contains an x-ray source and the mechanism for rotating the source about lateral and vertical axes. This view also shows a fragment of a longitudinally extending patient supporting table top mounted on the housing and a fragment of an x-ray image intensifier displaced vertically above the table top;

FIG. 8 is a diagram showing how the x-ray tube target is oriented relative to an image intensifier for obtaining oblique views of a heart.

DESCRIPTION OF A PREFERRED EMBODIMENT

Figure 1:
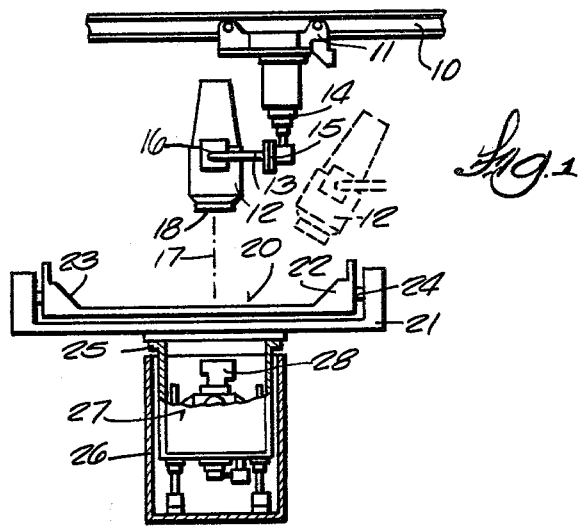
FIG. 1 is a front elevational view, partly in section, of a typical cardiovascular examination apparatus incorporating the modifications for enabling oblique x-ray views of the cardiovascular system to be obtained.

FIG. 1 shows a general view of one type of cardiovascular examination equipment which, in accordance with the invention, is adapted for obtaining oblique x-ray views of a patient's cardiovascular system without requiring rotation of the patient for every type of view required.

FIG. 1 shows a longitudinally extending track 10 on which a carriage 11 is mounted for rolling in opposite directions on the track. An image intensifier assembly 12 is mounted to the carriage by means of a horizontally oriented arm 13 which fastens to a vertically extensible and retractable column or telescoping device 14. Arm 13 is fastened to telescoping arm 14 through a coupling 15 which, in accordance with the invention, permits the image intensifier to be rotated through a limited angle about a horizontal axis. The means for locking coupling 15 and, hence, image intensifier 12 in definite lateral angle positions are not shown since they can easily be devised by those skilled in the mechanical arts.

The image intensifier can also be tilted or angulated caudally and cranially, that is, in the longitudinal direction relative to vertical about an axis extending perpendicular to the drawing through the point marked 16. The motor means for driving the image intensifier 12 angularly about laterally extending axis 16 is not shown in FIG. 1 but may be seen in cited U.S. Pat. No. 4,024,403 which is incorporated herein by reference. As shown in solid lines in FIG. 1, image intensifier 12 is oriented vertically which means that it is aimed in the direction of a vertical line 17 which is perpendicular to the image input plane 18 of the intensifier which input plane is presently in a horizontal orientation. Line 17 can also be looked upon as being coincident with the central ray of the x-ray beam. A dashed line representation of the intensifier shows it translated horizontally and angulated caudally, that is, toward the feet of a patient undergoing examination. The x-ray source, as will be evident later will be angulated oppositely or toward the head of the patient.

In FIG. 1, a patient who is to undergo a cardiovascular x-ray examination is normally supported in a cradle which is designated generally by the reference numeral 20. The usual procedure during an examination is to have the head of a supine patient at the end of the cradle marked 22 and the feet at the end marked 23. Cradle 20 is supported on shafts such as the one marked 24 so the patient may be revolved through a limited angle about the longitudinally extending axis of shaft 24 and held in any desired rotational position in the path of an x-ray beam which is projected through the patient to the input plane 18 of the image intensifier.

Patient supporting cradle 21 is mounted on top of an enclosure 25 which is vertically movable in a floor mounted housing 26. Part of an x-ray tube casing 27 is also visible in FIG. 1. The x-ray tube casing has a collimator 28 coupled with it for limiting the boundaries of the diverging x-ray beam which is emitted from the x-ray tube target in the casing to the boundaries of the input plane 18 of the x-ray image intensifier.

Referring to FIG. 2, x-ray tube casing 27 is supported on a base or stand 32 for rotating or angulating through a limited angle about a laterally extending axis which is perpendicular to the plane of the drawing and passes through the point marked 33. The motor means for angulating the x-ray tube casing 27 about the laterally extending axis 33 is not shown nor is the motor control shown. The motor and control are, however, shown in the cited patent. It is sufficient for present purposes to be aware that tube casing 27 is angulated coordinately or synchronously with image intensifier 12 so that the central ray 17 of the x-ray beam always remains perpendicular to the input plane 18 of image intensifier 12. There is an x-ray tube, of course, in x-ray tube casing 27. In FIG. 2, and some other figures as well, the glass envelope of the x-ray tube is not shown. The cathode structure of the x-ray tube is depicted in dashed lines and designated generally by the reference numeral 34. The rotating target disk is marked 35. Target disk 35 is displaced longitudinally from laterally extending tube casing tilt axis 33. The target has a beveled annular focal track surface on which the electron beam from cathode 34 is focused to a focal spot 36 on the x-ray tube target from which the x-ray beam is projected through collimator 28 so its central ray 17 will be perpendicular to the image input plane of the image intensifier at all times.

Enclosure 25 for the x-ray tube casing is comprised of longitudinally spaced apart x-ray impervious walls 37 and 38, a rear wall 39 and a front wall, which would be nearest to the observer in FIG. 2 but which has been omitted from that figure. Enclosure 25 also has a bottom wall 40 on which internally threaded collars 41 and 42 are fastened. Actually, there are four such collars, one at each corner of the bottom 40 of enclosure 25. Lead screws, such as the pair marked 43 and 44 thread into these collars and each lead screw is driven from a gear box such as those marked 45 and 46. The lead screws are driven by a motor 47 through a speed reducer 48 whose output shafts 49 and 50 transmit power to the gear boxes 45 and 46. It will be evident that when the lead screws are turned in one direction by reversible motor 47, enclosure 25, x-ray casing 27 in it, and the patient supporting frame 21 will go up or down depending on the direction in which the motor 47 is rotating. This, as is well-known, permits obtaining different amounts of magnification of the x-ray image impinging on input plane 18 of the intensifier.

The components of the system which have been described thus far correspond with the components and capabilities of the cardiovascular examination apparatus illustrated in the cited patent. To summarize, the x-ray tube casing 27 and, hence, the focal spot 36 of the x-ray tube can be rotated or tilted about the laterally extending axis 33 in a single longitudinally extending plane synchronously with the x-ray image intensifier to permit obtaining angular views of the heart in a longitudinal aspect. In the apparatus of the cited patent, the x-ray tube and intensifier can be tilted about 40° from vertical in the caudal direction, which is the direction in which the intensifier is tilted in the dashed line illustration of FIG. 1, to obtain views perpendicular to the plane in which certain blood vessels lie on the surface of the heart. As indicated earlier, however, it is sometimes advantageous to direct the x-ray beam obliquely through a patient's body when studying the heart in order to get the best view of the arteries surrounding it. Customarily, the desired view is one taken at 40° cranial and 20° right anterior oblique. In other words, the x-ray beam is not only at 40° from vertical in the longitudinal direction but is also 20° from vertical in the lateral direction. The improvements in the apparatus for making oblique views with the type of apparatus here under discussion without necessitating patient rotation will now be discussed.

To enable taking oblique views, the base 32 for supporting the x-ray tube casing 27 is adapted for rotation or angulation about a vertical axis as well as about a laterally extending axis 33. To achieve this objective as can be seen in FIG. 2, the base 32 which supports the x-ray tube casing 27 for longitudinal angulation is mounted on a vertical thrust bearing 55 which is secured to the bottom wall 40 of enclosure 25 with a clamping ring 56. Base 32 is coupled to a vertically oriented shaft 57 driven through a speed reducer 58 which is coupled to a reversible electric motor 59. Shaft 57 is fastened to base 32 with a flange 60, shown in dashed lines, and which is bolted to the base. Motor 59 is fastened to bottom plate 40 of vertically movable enclosure 25 so the motor rides up and down with the lead screw driven enclosure. The vertical axis of shaft 57 preferably extends through laterally extending axis 33 on which the x-ray tube casing 27 tilts longitudinally. The x-ray tube target focal spot 36 is displaced radially from the vertical axis of shaft 57 as well as from the horizontal axis 33 for the tube casing. Axes 57 and 33 intersect perpendicularly.

Figure 3:
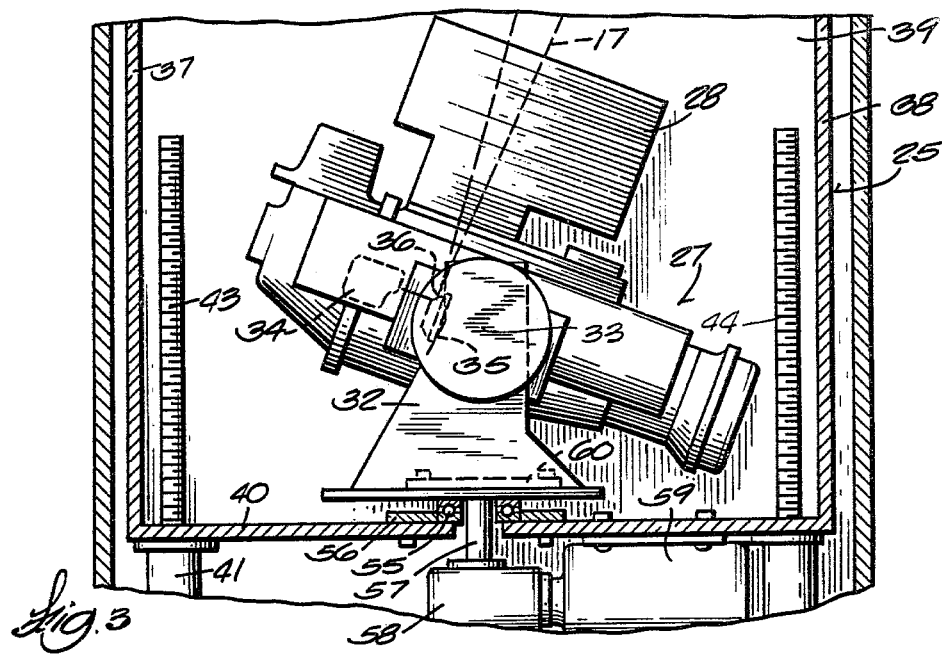
FIG. 3 shows the x-ray source angulated solely about its laterally extended axis.

FIG. 3 shows the tube casing 27 tilted in the cranial direction. The maximum amount of tilt of the central ray 34 of the x-ray beam is about 40° from vertical in the cranial direction. This longitudinal tilt was obtainable in the cardiovascular examination apparatus shown in the referenced patent and is representative of tilting the x-ray tube in a single longitudinally extending plane.

Figure 4:
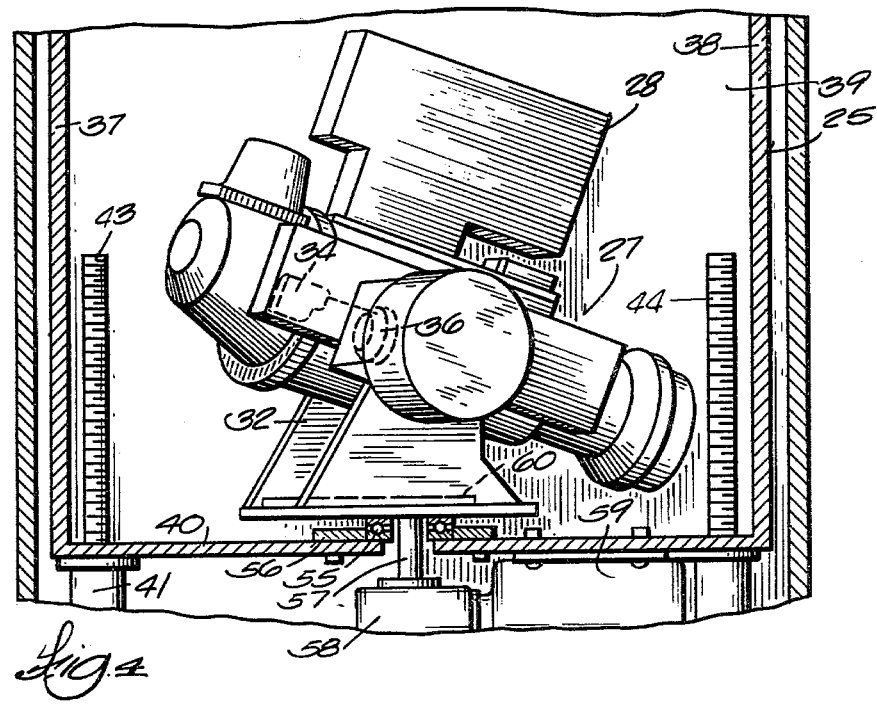
FIG. 4 shows the x-ray source angulated about its laterally extending axis and about a vertical axis also.

FIG. 4 shows the x-ray tube casing 27 after it has been rotated by operation of motor 59. The tube casing is also angulated generally longitudinally but the focal spot 36 on the x-ray tube target is now brought closer to the observer in FIG. 4. The focal spot is put in a position of displacement toward the side of the patient and elevated so that the x-ray beam may be projected upwardly longitudinally and obliquely without being cut off in part by any obstruction on the front or rear side members which bridge across the enclosure 25 immediately under table support 21, see FIG. 2, where a longitudinally directed and what would otherwise be an x-ray beam obstructing member of this type is marked with the numeral 61.

Figures 5, 6:
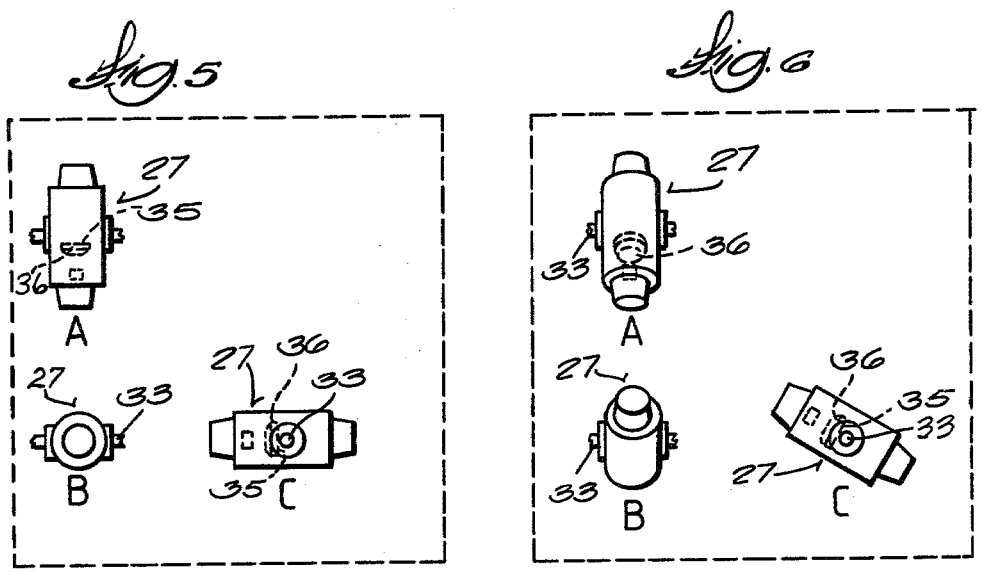
FIGS. 5, 6 and 7, respectively, are diagrams of the x-ray source in various angular positions.
Figure 7:
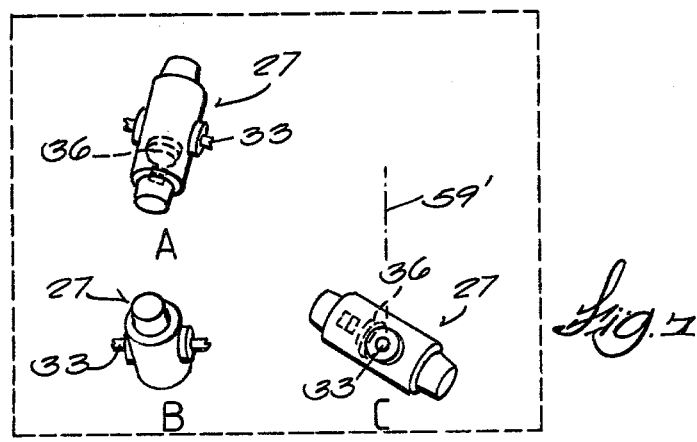

What is achieved by angulation of the x-ray tube focal spot about lateral axis 33 and the vertical axis of shaft 57 can be appreciated by considering the diagram shown in FIGS. 5-7. Part C of FIG. 5 shows a side elevation of the x-ray tube casing 27 and the target 35 inside of it while the x-ray tube is not angulated but is oriented for taking a direct vertical view, that is, with the focal spot 36 on the x-ray tube target directly under the center of the image input plane 18 of the image intensifier. Parts B and A of FIG. 5 simply show left end and top views, respectively, of the casing shown in part C.

In part C of FIG. 6, x-ray tube casing 27 is simply angulated longitudinally about lateral axis 33 in a single longitudinally extending vertical plane. As has been explained, when the x-ray tube casing is tilted solely on lateral axis 33 as in FIG. 6, and the image intensifier is tilted correspondingly, a longitudinal view in one plane is obtainable but an oblique view of the blood vessels in the heart is not obtainable. Parts A and B of FIG. 6 again show end and top views of the casing when it is tilted on one axis only as is the case in the side view identified as part C.

Part C of FIG. 7 shows the x-ray tube casing tilted about lateral axis 33 and also rotated about vertical axis 59' which is the vertical axis of shaft 59. In this case, the focal spot 36 on the x-ray tube target is displaced away from the observer and disposed in a position where it can permit the x-ray beam to be directed obliquely at the patient's heart. The fact that the focal spot 36 is radially displaced from both axes 33 and 59' permits the oblique angle to be obtained. By elevating the x-ray tube casing with the enclosure 25, the focal spot can be positioned where it will clear any obstruction around the top of the enclosure. In an actual embodiment, the arrangement is such that a 20° oblique angle can be obtained.

Parts B and A, respectively, simply show end and top views of the tube casing 27 when it is double angulated as in part C of FIG. 7.

FIG. 8 shows a relationship of the x-ray tube target 35, the heart 65 of a patient 66 and the input plane 18 of image intensifier 12 when the target is double angulated as in FIGS. 7 and 4. Here the focal spot 36 is shifted toward the observer from a vertical plane that would pass through and be coincident with a line 67 passing longitudinally through the patient. The axis of the x-ray target 35 is also tilted or angulated about lateral axis 33 so in combination with vertical rotation, the target 35 is positioned for having the diverging x-ray beam impinge obliquely on heart 65 instead of having the target lie in the same plane as axis 67 as would have been necessary before rotation of the target about a vertical axis was perceived as embodied in the cardiovascular examination apparatus described herein.

I claim:

1. Apparatus for making x-ray cardiovascular examinations comprising:
    an overhead carriage movable horizontally in opposite longitudinal directions,
    an x-ray image receiver and means for mounting said receiver to move vertically and to tilt in a single vertical plane through opposite angles from vertical about a first laterally extending axis that is transverse to the longitudinal direction,
    a longitudinally extending x-ray transmissive table top located below said receiver to support a body for examination and housing means below said table top, said housing means being adapted for mounting fixedly on a floor and comprising opposed pairs of side walls defining a top opening,
    enclosure means mounted for moving vertically within said housing, and comprising a bottom member and opposed pairs of side walls joined to said bottom member, said walls defining a top opening across which said x-ray transmissive table top extends for being supported from said side walls,
    an x-ray tube casing in said enclosure means and a base supporting said tube casing for tilting in said single vertical plane through opposite angles from vertical about a second laterally extending axis in opposite angular correspondence with said image receiver,
    a rotary anode x-ray tube in said casing having an x-ray target disk rotatable about a generally longitudinally directed axis, said disk having a beveled annular focal spot track surface on one of its faces and said disk being offset generally longitudinally from said second laterally extending axis to thereby offset the focal spot to one side of said second axis, the central ray of the x-ray beam emanating from said focal spot being moved in said single plane for all corresponding tilting angles of said x-ray tube and said image receiver, and
    the improvement for enabling said x-ray beam to be directed obliquely to said plane comprising,
    bearing means interposed between said base and said bottom member of the vertically movable enclosure, said bearing means supporting said base and x-ray tube casing thereon for rotation about a vertical axis, motor means mounted to said enclosure and means for coupling said motor means in driving relation to said base to effect rotation of the base about said vertical axis and thereby enable said tube casing to tilt in a vertical plane which is at an angle relative to the aforementioned vertical plane and to simultaneously offset said focal spot in a lateral direction so the central ray of said x-ray beam will be directed obliquely to said aforementioned plane.

2. The apparatus as in claim 1 wherein said means for mounting said image receiver includes means for enabling said image intensifier to tilt in a laterally extending plane through an angle corresponding with the oblique angle of said x-ray beam.

3. The apparatus as in claim 1 wherein said focal spot is offsettable in said lateral direction by rotation about said vertical axis by an amount which will permit an oblique angle of up to 20° to be obtained when said tubing casing is simultaneously tilted through an angle of about 40°.

* * * * *